United States Patent [19]
Shikinami et al.

[11] Patent Number: 5,723,145
[45] Date of Patent: Mar. 3, 1998

[54] TRANSDERMAL ABSORPTION PREPARATION

[75] Inventors: Yasuo Shikinami; Kunihiro Hata; Seiei Sasatani; Masao Sudoh, all of Osaka, Japan

[73] Assignees: Takiron Co., Ltd.; Ono Pharmaceutical Co., Ltd., both of Osaka, Japan

[21] Appl. No.: 898,646

[22] Filed: Jul. 22, 1997

Related U.S. Application Data

[63] Continuation of Ser. No. 716,047, Sep. 19, 1996, abandoned, which is a continuation of Ser. No. 448,614, filed as JP95/01584 Sep. 27, 1994, published as WO95/09008 Apr. 6, 1995, abandoned.

Foreign Application Priority Data

Sep. 30, 1993 [JP] Japan ................... 5-269842

[51] Int. Cl.$^6$ ................... A61F 13/02
[52] U.S. Cl. ................... 424/448; 424/449
[58] Field of Search ................... 424/448, 449

References Cited

U.S. PATENT DOCUMENTS 4,997,656  3/1991  Shikinami ................... 424/448

FOREIGN PATENT DOCUMENTS

| 0299758 | 1/1989 | European Pat. Off. . | |
|---|---|---|---|
| 63-108019 | 5/1988 | Japan | C08G 18/48 |
| 63-146812 | 6/1988 | Japan | A61K 9/70 |

*Primary Examiner*—D. Gabrielle Phelan
*Attorney, Agent, or Firm*—Sughrue, Mion, Zinn, Macpeak & Seas, PLLC

[57] ABSTRACT

The present invention provides a transdermal absorption preparation whereby a drug, which takes effect with a small amount, and is liable to be decomposed, solid at ordinary temperatures, water-soluble and less absorbable into the skin, can be stored stably for a long period of time and, can be transdermally administered at a high releasing ratio and yet releasing slowly, when applied to the skin. The constitution of the present invention is as follows: a transdermal absorption preparation which comprises a drug-storing layer containing a drug and having a drug-releasing face coated with a drug-releasing controlling membrane, wherein said drug-storing layer comprises as a base a heat-sensitive segmented polyurethane represented by the general formula:

$$R-A-(U)-F-(U)-B-R'$$

wherein A and B each represents a polymer of ethylene oxide, propylene oxide, tetramethylene oxide or 1,2-butylene oxide, or a random or block copolymer thereof, R and R' each represents a terminal H, $CH_3$, $C_2H_5$, $C_3H_7$ or $C_4H_9$, A=B or A≠B, R=R' or R≠R', F represents a constituting structure which is a moiety of a diisocyanate compound excluding two isocyanate groups, and (U) represents a urethane bond, and at least one of A and B is hydrophilic and at the same time at least one of A and B has a characteristic that it melts near the temperature of human skin, and wherein said drug-releasing controlling membrane is a phase-separated membrane comprising a mixture of a crosslinked gelatin phase and the uncrosslinked segmented polyurethane phase.

8 Claims, 2 Drawing Sheets

□ : POLYMER OF EXAMPLE 3 IN JP-A-63-146812
▲ : POLYMER OF EXAMPLE 2 IN JP-A-63-146812
● : POLYMER OF EXAMPLE 1 OF THE PRESENT INVENTION

TRANSDERMAL ABSORPTION PREPARATION

This is a Continuation of application Ser. No. 08/716,047 filed Sep. 19, 1996, now abandoned, which in turn is a Continuation of Ser. No. 08/448,614, filed May 26, 1995, now abandoned, which is a 371 of PCT/JP94/01584, filed Sep. 27, 1994, published as WO95/09008 Apr. 6, 1995.

TECHNICAL FIELD

This invention relates to a transdermal absorption preparation which is a system for slowly releasing a drug into the body through the skin (TTS; Transdermal Therapeutic System).

TECHNICAL BACKGROUND

In general, methods for administering drugs may be classified into (1) transmucosal administration (via digestive or respiratory organs, intranasal, intrabuccal, sublingual, intraocular, or anal), (2) injection (intravenous, subcutaneous, intramuscular), and (3) transdermal administration. Among these methods, the skin has been used for a long time as the administration site for drugs and there are a number of preparations therefor (for example, ointments, pastes, liniments, lotions, etc.). However, these preparations mainly aim at taking effects locally at the administration site.

In recent years, therefore, a transdermal therapeutic system (TTS), which is one of drug delivery systems (DDS), has been developed in order to deliver a drug to the systemic circulatory system.

Compared with injections and oral preparations, the transdermal absorption preparation of this system has the following advantages. (1) The drug concentration in the blood can be maintained at a constant level for a definite period of time, thus giving a sustained effect. (2) The first pass metabolism in the digestive tracts and the liver can be avoided. (3) It suffers from neither any damages in the digestive tracts caused by oral preparations nor any pain or tissue damages due to injections, and it does not require regular outpatient treatment but is usable in home treatment. (4) The application frequency can be lowered and, as a result, compliance can be improved. (5) It can be peeled off anytime to thereby cease the absorption after administration, which makes it easy to avoid the occurrence of side effects and excessive administration. (6) A drug having a short half-life can be continuously administered.

Because of these advantages, it was once considered as technically possible and meaningful to apply the TTS to any drug and thus studies were extensively carried out for this purpose. However, the following requirements should be satisfied for applying TTS. (1) The drug has a small molecular weight and a low melting point. (2) It has a time-dependent effect. (3) It has a low effective concentration in the plasma. (4) The change in the dosage form contributes to the solution of the problems actually encountering in the conventional injections or oral preparations.

In addition, the skin has some problems as an administration site. For example, (1) drugs, in particular, water-soluble ones hardly permeate into the skin or are hardly absorbed. (2) The release and absorption of drugs are liable to vary depending on the site and damaged conditions of the skin and from individual to individual. (3) There is a risk that repeated applications to a skin site may cause inflammation. (4) There is a possibility that drug-metabolizing enzymes contained in the skin may inactivate drugs. In addition, there are other problems that it is highly difficult to manufacture a preparation wherein a drug which has a short half-life and easily undergoes decomposition can be maintained in a stable state. The development of TTS is hindered by these problems.

Drugs which have been practically employed in transdermal absorption preparations aiming at delivering the drug to the systemic circulatory system are limited ones, such as scopolamine for preventing motion sickness, nitroglycerin and isosorbide dinitrate for treating angina pectoris, clonidine for treating hypertension, estradiol for relieving follicular hormone depression and nicotine for preventing smoking.

The drug-storing layers of transdermal absorption preparations which are put into a practical use can be roughly classified from the standpoint of storage and release of drugs into (1) a reservoir type, (2) a matrix type, (3) a pressure-sensitive adhesive (autohesion) tape, (4) a multilayer adhesive tape, and (5) others. Each of the drug-storing layers uses, as a base thereof, a silicone oil in (1), a hydrophilic polymer such as polyvinyl alcohol (PVA), polyvinylpyrrolidone (PVP), etc., or a silicone elastomer in (2), and an acrylate type adhesive (PSA) in (3). The above-described (4) includes a preparation in which adhesive layers having different affinities to the drug are overlaid in a multilayer so as to control a releasing property. In addition, transdermal absorption preparations having various polymers such as a natural rubber, synthetic rubbers, cellulose, synthetic resins, etc. as the base for the drug-storing layer are now under investigation.

A drug-storing layer in the above-described transdermal absorption preparations (1) and (2) is generally coated with a drug-releasing controlling membrane (a drug permeation membrane). As this drug-releasing controlling membrane, a polymer membrane of an ethylene/vinyl acetate copolymer, an acrylic resin, a polyethylene, ethyl cellulose, etc., and a porous membrane thereof are used. In particular, a gelatin membrane discussed by the present inventors in JP-A-63-146812 (U.S. Pat. No. 4,997,656; the term "JP-A" as used herein means an "unexamined published Japanese patent application") is not irritative to the skin and causes no inflammation and, from this standpoint, is considered to be superior to the above-described polymer membranes.

The purpose of ordinary transdermal absorption preparations is to naturally diffuse the drug in the base and to distribute and transfer the drug to the skin side and allow the drug to be absorbed by the living body upon merely adhering the preparation to the skin surface by utilizing the concentration gradient of the drug as a driving power for the diffusion and release without depending upon a method of applying an external energy such as electricity or ultrasonic wave. Thus, the use of the ordinary transdermal absorption preparation is convenient. In order to achieve the above purpose, it is necessary that the base of the drug-storing layer has at least the following chemical and morphological characteristics.

(a) The base and the drug are required to have an appropriate affinity (compatibility). The term "appropriate" used herein means that the affinity is such a degree that the drug is capable of leaving the base and transferring to the skin. The releasing ratio of the drug varies remarkably depending upon the above affinity, and also the 0 order release is obtainable.

(b) The base is required to be a liquid at ordinary temperatures or, apparently, to be in an intermediate form between solid and liquid states such as a swollen gel which is a liquid-containing form, so that the drug (in particular, a solid drug) can diffuse in the base. In the reservoir type practically used, a silicone oil which is a liquid is used, and in the matrix type, a hydrogel of a water-soluble polymer is used. Also, when a silicone elastomer which is a rubbery polymer is used, the drug is dispersed therein together with a solvent. In the case of an adhesive tape, a tackifier is dispersed as a liquid in an adhesive, and the adhesive per se is a gel which is in an intermediate region between solid and liquid forms. These facts satisfy the above-described requirements of the base.

However, the type wherein the drug is supported in the adhesive does not generally have a relatively high releasing ratio of the drug. Also, although an oily or aqueous swollen gel has the releasing ratio slightly higher than that of the above type, some drugs may have problems in the storage stability when a preparation is produced by using the swollen gel. More specifically, there are possibility of changes in the initial dose of the drug due to release of a solvent or water as a swelling medium with the passage of time, as well as the modification of the drug by a reaction with a dispersing medium. Further, in the case of the reservoir type wherein a liquid drug is blended in a liquid with a powdery material such as an emulsifying base, or wherein a solid drug is dispersed together with a liquid co-solvent, these components tend to transfer to the surface of the preparation during storage and hence it is unavoidable that the drug accumulates at a high concentration in the release-controlling membrane covering the base (i.e., a drug permeation membrane), and there may be a problem that the drug is drastically released at the initial stage of the application.

(c) The base is required to have a low irritation to the skin or substantially no irritation. Since the transdermal absorption preparation is generally replaced repeatedly, a skin inflammation causes a great problem. Thus, reduction in the size of the preparation is advantageous.

(d) Even if the drug takes effect with only a small dose of several micrograms and is unstable such that the drug is easily modified by air, moisture, heat, or the like, it is necessary that the drug can be stored stably and released at a high releasing ratio. The drug of which formulation into a transdermal absorption preparation is particularly significant is those having a high decomposition ratio in the digestive tract, liver, etc., a short half-life and a low effective serum concentration. Most of these drugs have the above-described characteristics and hence it is necessary to take any countermeasure thereto.

(e) Even if the drug is water-soluble and has poor permeability and absorption through the skin, it is necessary that the drug can be slowly released into the body at a high efficiency. It is desirable that the above can be achieved, in particular, without using an absorption enhancer, etc. Recently, studies on the absorption enhancer have been made extensively, but troublesome issues are involved therein such as the necessity of investigation on the toxicity of the enhancer itself.

For solving the above-described problems, the present inventors developed the transdermal absorption preparation described in JP-A-63-146812. That is, the base polymer as the drug-storing layer in this transdermal absorption preparation is a heat-sensitive and water-sensitive amphipathic polymer which is a segmented polyurethane in which block linkages are adjusted in such a manner that the hydrophilicity increases as the block comes close to one end of the polymer molecule and the hydrophobicity or lipophilicity increases as the block comes close to other end of the polymer molecule.

In the above amphipathic segmented polyurethane, a balance of hydrophilicity and the hydrophobicity and a molecular weight of constituting molecules of the segments are adjusted so that the polymer can dissolve or melt in response to water or heat. When it is dissolved or molten, the hydrophilic segment solubilizes a hydrophilic drug and the hydrophobic (lipophilic) segment solubilizes a hydrophobic (lipophilic) drug. Generally, drugs have a structure containing polar groups or non-polar groups and have hydrophilic, lipophilic or amphipathic characteristics and is dissolved in the same type of solvents. Even if the drug is exceptionally insoluble in solvents, the drug takes effect as long as it is dissolved in a very minute amount and, therefore, the drug may be investigated at a level of a very low solubility. Accordingly, the drug is necessarily assigned to any of the above-described groupings. Also, since the solubilization by this polymer makes it possible to dissolve the drug at a molecular level, i.e., as a molecular dispersion, it is particularly effective for slow-releasing of a physiologically active material which takes effect with a very minute dose of several micrograms per prescription. In other word, in order to store a drug which has a low effective serum concentration and which takes effect even with a very minute dose and to release the drug, dispersion of the drug at a molecular level is essential. Most of these physiologically active materials are also easily decomposed by oxygen, water, heat, etc. However, as the term "heat-sensitive property" connotes, the polymer keeps a solid state at ordinary temperatures below the temperature of human skin (i.e., below 30° C.) and hence the drug can be stably maintained in a solid. When applied to the surface of a living body, the polymer is easily transformed from a solid to a liquid by sharply responding to the temperature of the body surface. As the term "amphipathic" connotes, also, the polymer responds to water and thus the polymer is dissolved by a small amount of water exuded from the body surface, and the drug is diffused and transferred in the polymer and absorbed by the skin through the drug-permeation membrane on the surface. Although some drugs are in a liquid state at ordinary temperatures, most of drugs are in a solid state. In order to release a solid drug by diffusion in a base and to absorb the drug into the skin, the base must be either a liquid or a gel material. The above-mentioned polymer satisfies this requirement and can be used as a base polymer for a transdermal absorption preparation applicable to many drugs.

However, as a result of further studies, the present inventors found that a heat-sensitive polymer having a higher hydrophilicity is required for, among others, water-soluble drugs which are difficult to permeate into the skin. Also, it has been found that, in order to release these drugs efficiently within a short period of time, for example, a predetermined time of from 24 to 48 hours, the dissolved and molten polymer is required to have a lower viscosity and form an environment in which the drug is easily diffused.

In addition, with respect to the above-described polymer membranes which have been used as drug-releasing controlling membranes (drug permeation membranes) coating drug-storing layers, it is difficult to control the rate of transfer of a minute amount of a certain type of drugs in the membrane and to control its permeation amount. Therefore, they are scarcely applicable to transdermal absorption preparations wherein the amount of a drug in a minute amount to be absorbed by the skin should be strictly controlled. Thus, it is understood that a drug-releasing controlling membrane capable of regulating these factors at a high releasing ratio is necessary.

It is an object of the present invention to provide a transdermal absorption preparation whereby these requirements can be satisfied.

DISCLOSURE OF THE INVENTION

To achieve the above object, the present invention provides a transdermal absorption preparation which comprises a drug-storing layer containing a drug and having a drug-releasing face coated with a drug-releasing controlling membrane, wherein said drug-storing layer comprises as a base a heat-sensitive segmented polyurethane represented by the general formula:

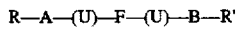

wherein A and B each represents a polymer of ethylene oxide, propylene oxide, tetramethylene oxide or 1,2-butylene oxide, or a random or block copolymer thereof, R and R' each represents a terminal H, $CH_3$, $C_2H_5$, $C_3H_7$ or $C_4H_9$, A=B or A≠B, R=R' or R≠R', F represents a constituting structure which is a moiety of a diisocyanate compound excluding two isocyanate groups, and (U) represents a urethane bond, and at least one of A and B is hydrophilic and at the same time at least one of A and B has a characteristic that it melts near the temperature of human skin (30° to 40° C.); and wherein said drug-releasing controlling membrane is a phase-separated membrane comprising a mixture of a crosslinked gelatin phase and said uncrosslinked segmented polyurethane phase.

Preferable embodiments of the transdermal absorption preparation of the present invention include those wherein, in the above general formula, (1) at least one of A and B is an ethylene oxide polymer, (2) one of A and B is an ethylene oxide polymer and another one is a tetramethylene oxide polymer, (3) one of A and B is an ethylene oxide polymer and another one is a butylene oxide polymer, (4) both of A and B are ethylene oxide polymers, (5) at least one of A and B is a random or block copolymer of ethylene oxide and propylene oxide, (6) one of A and B is an ethylene oxide polymer and another one is a random or block copolymer of ethylene oxide and propylene oxide, (7) the number-average molecular weight of each of the above-described ethylene oxide polymers range from 800 to 1,200, (8) the total molecular weight of the segmented polyurethane serving as the base of the drug-storing layer ranges from 1,000 to 6,000 as the number-average, and (9) the drug-releasing controlling membrane contains glycerin and/or polyglycerin.

FIG. 1 is a sectional view which shows the fundamental structure of the transdermal absorption preparation according to the present invention; and FIG. 2 is a top view of the same wherein 1 represents a surface layer, 2 represents a pressure-sensitive adhesive layer applied onto the surface layer, 3 represents a hard base, 4 represents a drug-storing layer, 5 represents a drug-releasing controlling membrane (phase-separated membrane) and 6 represents a liner.

The surface layer 1 and the hard base 3 sticking thereto serve as a support of the transdermal absorption preparation and prevent the moisture-absorption during storage as well as the bleed-through of the drug onto the opposite side to the skin. This surface layer 1 is made of a synthetic resin film of, for example, polyethylene, polypropylene, flexible polyvinylchloride, ethylene/vinyl acetate copolymer, ethylene/vinyl alcohol copolymer or polyethylene terephthalate. It is preferably made of a low-modulus material excellent in flexibility, stretchability, feel and texture (for example, a flexible polyurethane film, a flexible polyvinylchloride foam, an ethylene/vinyl acetate foam, a 1,2-polybutadiene foam or a moistureproof and gas-barrier non-woven fabric treated with a polymer film each having a 100% modulus of about 5 kg/cm² or below). Among these materials, a 1,2-polybutadiene foam may be cited as one causing no blocking, having a small thickness and a high safety without suffering from any bleed-through of a plasticizer. Thus, it is one of the most desirable materials. When easiness in handling are taken into consideration, the appropriate thickness of the surface layer is from 0.15 to 1.0 mm. It is sometimes possible that the front surface or the back surface of the material is treated with a surface-treating agent so as to slip and to prevent peeling-off, when it comes in contact with clothes, or to prevent the bleed-through of the drug or the adhesive onto the surface layer.

The hard base 3 applied onto this surface layer 1 via the pressure-sensitive adhesive layer 2 aims at preventing the transfer of the drug and the base, which serves as the drug-storing layer, toward the surface layer 1. When the skin moves, the flexible surface layer 1 presses this hard base 3 onto the skin and makes the preparation to closely stick thereto. Thus, it is another object of the hard base 3 to facilitate the transfer of the drug toward the skin. This hard base is made of a hard sheet or film of, for example, polyvinyl chloride, polyethylene terephthalate, polypropylene, polyethylene, polystyrene or polymethyl methacrylate.

The pressure-sensitive adhesive layer 2 contributes to the mutual sticking among the surface layer 1, the hard base 3 and the phase-separated membrane 5 serving as the drug-releasing controlling membrane and to the adhesion of the preparation to the human skin. By using the adhesive having hydrophilic or lipophilic characteristic contrary to a base and a drug, run-off of the polymer and the drug in the drug-storing layer 4 into the pressure-sensitive adhesive layer 2 can be prevented. It is also possible that a part coming into close contact with the skin is exclusively replaced with a material which is highly compatible with the skin. In general, acrylic or rubber pressure-sensitive adhesives can be used therefor. Alternatively, vegetable adhesives of polysaccharide type or adhesives from animals, such as gelatin, may optionally be employed therefor. The thickness of this adhesive layer 2 preferably ranges from about 20 to about 500 μm.

As the liner 6, a silicone-treated mold-release paper or a mold-release film commonly employed in the art may be used. This liner 6 is peeled off before the transdermal absorption preparation is applied onto the skin.

The transdermal absorption preparation according to the present invention is mainly characterized by the drug-storing layer 4 and the drug-releasing controlling membrane 5 (drug permeation membrane) coating the drug-releasing face of the drug-storing layer.

This drug-storing layer 4 has a novel segmented polyurethane represented by the above general formula as a base. Illustrative examples of the structure thereof are shown in Table 1 below.

TABLE 1

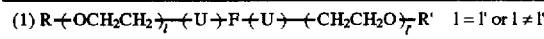

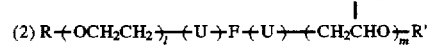

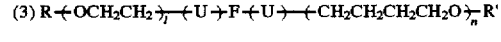

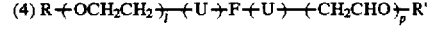

TABLE 1-continued (5) R─(EO)$_l$─(U)─F─(U)─(EO/PO)$_q$─R'

(6) R─(EO/PO)$_q$─(U)─F─(U)─(EO/PO)$_{q'}$─R'   q = q' or q ≠ q'

(7) R─(EO/PO)$_q$─(U)─F─(U)─(PO)$_m$─R'

(8) R─(EO/PO)$_q$─(U)─F─(U)─(TMO)$_r$─R'

(9) R─(EO/PO)$_q$─(U)─F─(U)─(BO)$_p$─R'

(10) R─(EO)$_l$─(U)─F─(U)─(EO/TMO)$_s$─R'

(11) R─(EO)$_l$─(U)─F─(U)─(EO/BO)$_t$─R'

(12) R─(EO/PO)$_q$─(U)─F─(U)─(EO/TMO)$_s$─R'

(13) R─(EO/PO)$_q$─(U)─F─(U)─(EO/BO)$_t$─R' wherein EO is —OCH$_2$CH$_2$—,

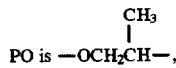
PO is —OCH$_2$CH—,

TMO is —CH$_2$CH$_2$CH$_2$CH$_2$O—,

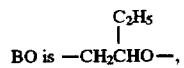
BO is —CH$_2$CHO—,

EO/PO, EO/TMO and EO/BO each represents a block or random copolymer thereof, —(U)— represents a urethane bond, F represents a structure of the moiety of the diisocyanate compound excluding two isocyanate groups (—NCO), l, l', m, n, p, q, q', r, s and t each represents a positive integer, and R and R' each represents H, CH$_3$, C$_2$H$_5$, C$_3$H$_7$ or C$_4$H$_9$.

In the segmented polyurethane of the above general formula, the necessity of at least one of A and B being hydrophilic is for the purpose of dissolving the hydrophilic drug in a relatively large amount, while the amount is a low concentration level at a degree of taking effect. The hydrophilic drug refers to the opposite of the lipophilic drug, and shows an affinity to water. Basically, the hydrophilic drug has a certain degree of solubility in water. Illustrative examples of the drug include prostaglandins, as will be described in detail hereinafter, nitroglycerin and attopine, as well as strophanthin, isoproterenol hydrochloride, oxprenolol hydrochloride, captopril, etc. Also, this segment provides a moisture (water) absorbability and is a basis for a water-sensitivity by which the polymer is easily dissolved in a very minute amount of water on the body surface. The water-sensitivity refers to a property of a sharp sensitivity to water in such a manner that the polymer itself has a moisture absorbability, dissolves upon absorption of a small amount of water (moisture), transforms from a solid to a liquid containing water by further absorbing water by itself, and, at the same time, a melting temperature thereof reduces. The basis for the hydrophilicity is an ether oxygen (—O—) in the molecular chain and —OH at a terminus of the molecular chain. Since —CH$_3$ and —C$_2$H$_5$ side chains attached to the methylene chain (—CH$_2$—) prevent an access of water to the ether oxygen, ethylene oxide which has no such side chain and which has a proportion that one ether oxygen exists per two methylene groups is, among others, most hydrophilic. Polymers having side chains are more hydrophobic, and the hydrophobicity increases, as the size of an alkyl side chain increases. Further, the terminal —OH shows hydrophilicity but, when an alkoxy terminus such as —OCH$_3$, —OC$_2$H$_5$, —OC$_3$H$_7$ or —OC$_4$H$_9$ is formed, the hydrophobicity increases depending on the order of size of the alkyl moiety shown herein. Accordingly, when the segments in both sides of the urethane bond are EO, the degree of hydrophilicity can be delicately adjusted by making the termini hydrophobic using the alkoxy termini.

In order to take advantage of the inherent property of the segment, an excessively long alkyl chain length in the alkoxy termini is not preferred since it affects the hydrophilicity of the whole molecule and also alters a melting temperature of the polymer from the inherent one. As one approach, the terminus can be a long alkyl chain or an ester bond with an aromatic carboxylic acid as in the conventionally used non-ionic surface active agents. However, in this case, due to an cohesive force of the ester bond, an interaction of the drug with the ester bond is involved in addition to the interaction between the ether bond in the segment and the drug and hence the control of slow-releasing becomes difficult. Also, similar to the case where the terminus is the alkoxy terminus obtained by using a long alkyl alcohol, the ester bond is considered to affect greatly the solidifying point and the amphipathicity, the alkoxy terminus obtained by using a short alkyl alcohol within the scope of the present invention is preferred.

Further, the degree of hydrophilicity (hydrophobicity) can be adjusted by using a segment of the above-described copolymer containing EO in proportion to a ratio of EO. From this viewpoint, a combination of segments on both sides of the diisocyanate compound can be illustrated as shown in Table 1.

The heat-sensitivity which causes transformation from a solid at ordinary temperature to a viscous liquid upon melting near the surface temperature of the human skin can be adjusted by a molecular weight of EO or tetramethylene oxide (TMO). However, when the viscosity in a molten state is considered, the heat-sensitivity is preferably adjusted by EO. The expression "near the surface temperature of the human skin" used herein means a temperature zone of from 30° to 40° C., while the expression "ordinary temperatures" as used herein means a temperature range which is not lower than 0° C. and lower than 30° C. The human skin temperature falls within a range of from 30° to 37° C. Alkylene oxides other than EO and TMO are liquid at ordinary temperatures and are not factors of the heat-sensitivity. Rather, the other alkylene oxides are expected to have a function as a hydrophobicity-providing segment of the amphipathicity and serves as a factor of an affinity to a hydrophobic drug. In the case of the copolymer containing EO, copolymers which satisfy the requirement for transformation by heat exist, depending upon a ratio and a molecular weight of EO, and a type of the copolymer (whether block or random) and a molecular weight of EO contained therein, but many of the copolymers have no definite solidifying and melting temperatures as compared with those of the polymer of EO alone. Also, these copolymers containing EO are not a crystalline hard solid and thus there is a problem in the use of such copolymers as a stable solid phase for storing the drug for a long period of time. Further, since such copolymers containing EO necessarily have relatively high molecular weights due to the necessity in the chemical structure thereof, the viscosity in the molten state is fairly high. Such a high viscosity is not preferred from the standpoint of diffusion of the drug, but the copolymers can be used depending upon the type of the drug (for example, more hydrophobic drugs).

An example having a polymer of EO alone in at least one of the segments is described hereinafter. In the polyethylene glycols which are polymers of EO alone, a number-average molecular weight of the material (polymer) which undergoes a solid-liquid transformation near the temperature of human skin surface, at 30° to 40° C., is about 800 to 1200 and, for example, a solidifying temperature of the material (polymer) having a number-average molecular weight of 1000 is 37.1° C. (the regulated value in *Pharmacopeia of Japan:* 35° to 39° C.), and thus that having a number-average molecular weight of from 800 to 1200 is preferably selected.

In the case of (1) in Table 1, when a number-average molecular weight of 1000 is used in either of EO segments, an average molecular weight of 200 to 1000 may be used in the other segment. Both termini can be an alkyl ether or —OH. These polymers may be selected depending on the properties of the drug. An attention should be paid to a solidifying point, for example, when segments of a number-average molecular weight of 1000 having a solidifying point of 37.1° C. are used in both segments. The solidifying point of the polymer having an average molecular weight of 2000 in the case where polyethylene glycols having an average molecular weight of 1000 are merely bonded is about 45° C., but the solidifying point in the above-described case is substantially the same as the solidifying point of the polymer having an average molecular weight of 1000. The solidifying point reduces by a degree of only about 1° to 2° C. depending upon the terminal alkyl group. This indicates that the structure of the diisocyanate compound as a spacer between the linked segments avoids the affects on the solidifying point caused by the EO chains in the polyethylene glycol, the length of the molecule and the intermolecular or intramolecular cohesive force produced by the terminal groups, whereby the intermolecular or intramolecular motion inherent to the segment are made independent and thus the solidifying point based on a number-average molecular weight of 1000 appears substantially as it is. The above facts are the basis for designing the polymer molecule satisfying the object of the present invention. That is, even when the total molecular weight becomes large, the solidifying point thereof remains at a temperature near that of the constituting segments and thus it is possible that one of the segments is provided with others functions.

The construction of (2) in Table 1 is an example in which a propylene oxide (PO) chain is introduced in one of the segments, and the PO chain is relatively hydrophobic due to —CH₃ present in the side chain. However, if the molecular weight is several hundreds or below and the terminal —OH remains, a hydrophilic characteristic still remains due to the effect of this hydroxyl group. Accordingly, in the case of (2) in which the EO segment is present in one side, a molecular weight of the PO segment of up to about 1000 is used. This is also a limitation of the length with consideration of the melt viscosity.

The constructions (3) and (4) in Table 1 are examples having more hydrophobic segments in one side and are useful for a hydrophobic drug. The molecular weight of these segments is suitably up to a number average molecular weight of about 1500, preferably from about 300 to about 1500, with consideration of the same factor as in (2).

The construction (5) in Table 1 is the case using an EO/PO copolymer in one side. Although a degree of hydrophilicity and hydrophobicity varies depending upon the ratio and the molecular weight of the EO and the type of copolymer, the polymer can be adjusted to be more hydrophobic than the case in which the both segments are EO polymers and can be adjusted to be more hydrophilic than the case of (2). Also, its melt viscosity is between the cases of (1) and (2). Copolymers are commonly inferior in the crystallinity to a homopolymer. Accordingly, when a crystalline segment of the EO polymer is used in one side, the heat-sensitivity thereof varies sharply. Also, in the case of a random copolymer, the molecular motion of the molecular units randomly arranged in the random copolymer, particularly an actively moving characteristic of the small units therein, provides desirable results to the diffusion and the release of the drug, etc.

Further, in the case of (5) and the subsequent polymers, the molar ratio of EO and the other component in the copolymer containing EO is appropriately selected so that the molar ratio of EO falls in the range of 10 to 90%, preferably 30 to 70%.

The above-described facts are similarly applied to the combination of (6) and the subsequent polymers in Table 1 and, with consideration of characteristics of drugs, etc. and releasing patterns required for drugs, etc., a combination of these segments can be selected. Also, the type of the terminal groups can be selected in a similar manner.

The total molecular weight of the polymers represented by these structural formulae varies depending upon the combination of each of the segments, but is approximately from 1000 to 6000, preferably from 1200 to 2500.

The diisocyanate having the structure of the intervening F in the above-described general formula can be selected from p-phenylene diisocyanate, 2,4-toluylene diisocyanate (TDI), 4,4-diphenylmethane diisocyanate (MDI), naphthalene 1,5-diisocyanate, hexamethylene diisocyanate, tetramethylene diisocyanate, lysine diisocyanate, xylylene diisocyanate and hydrogenated TDI, hydrogenated MDI, dicyclohexyldimethylmethane p,p'-diisocyanate, isophorone diisocyanate, etc. However, since a structure in which the both segments are extending linearly tends to exhibit a heat-sensitivity more sharply and to have a low melt viscosity, a diisocyanate having a linear structure is desirable and also an aliphatic diisocyanate is more preferred than an aromatic or alicyclic diisocyanate in view of ease in molecular motion. A polyfunctional compound such as a triisocyanate may be used, but is not preferred since the melt viscosity thereof becomes generally high.

The cohesive force of the urethane bond (—NH—COO—) formed by the reaction between such a diisocyanate and an alkylene glycol is 8.74 (kcal/mol). Since this value is high as compared with 0.68 for —CH₂—, 1.36 for —CH (CH₃)—, 1.77 for —CH₃ and 1.00 for —O— which are constituting unit molecules of alkylene glycols and functions to increase the melt viscosity, it is convenient for adjusting a viscosity to a preferable degree for a drug storing layer. In fact, the polymer according to the present invention having these intervening urethane bonds has a melt viscosity slightly higher than that of an alkylene glycol having the same molecular weight and, therefore, is effective for delicately controlling the drug releasing. If the melt viscosity is too low, it is not preferred since the polymer flows down from the skin. Also, urethane molecule between both side urethane bonds have an appropriate molecular length suitable as a spacer between the both segments and have a suitable function for an independent molecular motion of each segment.

The segmented polyurethane having the above-described structure can be synthesized by, for example, the following method. First, polyalkylene glycols respectively having the segments A and B in the above general formula are dehydrated and dried at 60° C. under reduced pressure by using a vacuum dryer. After measuring the OH values of these polyalkylene glycols and the NCO value of the diisocyanate having the structure F of the above general formula by conventional methods, the polyalkylene glycols of A and B and the above-described diisocyanate F are mixed together in such a manner as to give a molar ratio of 1:1:1 and reacted in an inert gas (for example, $N_2$) atmosphere at 70° C. by using a catalyst such as di-n-butyltin dilaurate or without using any catalyst. In this case, the reaction is carried out while dropping the diisocyanate F into the polyalkylene glycols of A and B. The end point of the reaction is assumed by IR absorption spectrum when an absorption at 2250 cm$^{-1}$ by the isocyanate group disappears.

A drug may be incorporated into this segmented polyurethane by heating the polymer to 40° to 60° C. to thereby melt the same and adding a definite amount of the drug thereto followed by dissolution or dispersion by mixing and stirring. When the polymer has a relatively high melt viscosity, the dissolution can be achieved within a short period of time by adding a solvent both for the drug and the polymer. Next, the solvent may be removed by evaporation under reduced pressure.

Next, the drug-releasing controlling membrane 5 will be explained. As FIG. 3 shows, this drug-releasing controlling membrane 5 is a phase-separated membrane (a membrane having separated phases) comprising a mixture of a crosslinked gelatin phase 5a and an uncrosslinked segmented polyurethane phase 5b.

Generally, a phase-separated membrane means a membrane in a state where two or more different phases are present in the membrane as a mixture. An interface of the phases is physically weak, and permeation is considered occur from the boundary. The phase transition of the mixed polymer system proceeds over a broad temperature range, and the polymer having a higher crystallization temperature (Tc) tends to cause the phase-separation earlier.

Polymer alloys which are multi-component polymer systems comprising a combination of chemically different polymers are classified into a group having a micro-phase-separated structure of a block or graft copolymer in which heterogeneous polymers are linked through a covalent bond, and a group of a polymer blend having a phase-separated structure in which heterogeneous polymers are present as a mixture in a macro-phase. The phase-separated membrane employed as the drug-releasing controlling membrane 5 in the present invention belongs to the latter polymer blend. The membrane can be obtained by the solution-cast blends method in which the membrane is made by casting of a solution in water which is a solvent for both of the gelatin and the segmented polyurethane.

Generally, in an amorphous polymer blend system, a phase separation showing the phase pattern of LCST type (a lower critical solution temperature) and UCST type (an upper critical solution temperature) occurs. In this case, the phase pattern of a two-component system of a liquid/liquid phase separation type is separated by a binodal curve connecting the cloud points and a spinodal curve connecting the changes in the free energy curve of blend. The inside of the spinodal curve is an unstable area, and the presence of even slight fluctuation in the concentration causes a reduction in the free energy and the phase separation proceeds. This phase separation is called "spinodal decomposition (SD)".

In the case of physical blends such as the above-described solution-cast blends, their components are rarely mixed uniformly and adhesion of the both components is poor and, hence, a material (membrane) of good quality cannot be obtained unless the both components are blended as uniformly as possible. Accordingly, polymers having a certain degree of miscibility with each other are selected for the components. An aqueous solution of gelatin and an amphipathic (hydrophilic) segmented polyurethane of the present invention forms a metastable compatible region between the binodal curve and the spinodal curve, and this promotes a stable and a certain degree of nucleation and growth (NG) by an increase in the concentration of the both components in the progress of water evaporation. The metastable phase separation structure generated by the NG mechanism and the SD in the above progress depends upon a water evaporation rate, a cooling rate and a viscosity change in the system, and is not determined only by thermodynamic properties of the system. In summary, the progress of the formation of the phase-separated membrane according to the present invention can be effected by, in principle, the spinodal decomposition by the solution-cast blends method.

To describe more specifically, the gelatin phase 5a of the phase-separated membrane forms a skeleton of the membrane and is present at a proportion of at least 40%, preferably from 60 to 80% based on the total weight of the membrane, and forms a three-dimensionally continued phase. On the other hand, the segmented polyurethane phase 5b plays a role of pathway which predominantly permeates drugs and other chemical substances and is present at a proportion of 60% or less, and preferably from 20 to 40%, based on the total weight of the membrane, and forms a continuous phase at least in the thickness direction of the membrane.

It is necessary that the above-described gelatin phase 5a has been made water-insoluble by crosslinking. The reason is that, if the gelatin phase 5a is uncrosslinked, it is dissolved by moisture exuded from the skin upon application of this phase-separated membrane to the skin after peeling off the liner 6 and the shape of the membrane cannot be sustained. However, the segmented polyurethane phase 5b should be uncrosslinked and must retain its fluidity. If the segmented polyurethane phase 5b is crosslinked, it becomes a gel or solid state and is unable to move by its melting and fluidity and, hence, the immersion and the permeating movement of the drug, etc. are disturbed. The term "crosslinked" as used herein means that the molecular chain is in a three-dimensional form to a degree of water-insoluble state, and the term "uncrosslinked" as used herein means that the molecular chain is linear and is not a three-dimensional form at all.

The segmented polyurethane phase 5b must be a solid state at an ordinary temperature. If the segmented polyurethane is a liquid state at the ordinary temperature, it bleeds out from the phase-separated membrane. However, if the segmented polyurethane phase 5b is in a solid state when the phase-separated membrane comes in contact with the skin, it is fixed in the phase-separated membrane without bleeding out, and immersion and permeation of drugs becomes difficult and the membrane substantially does not function as a permeation membrane for a minute amount of drugs. Accordingly, it is necessary that the segmented polyurethane phase 5b is molten to a liquid state at from 30° to 40° C. which is near the skin temperature of human. Such a segmented polyurethane phase 5b which is solid at ordinary temperatures and is molten at from 30° to 40° C. to a liquid state can be prepared by adjusting the molecular weight of the segmented polyurethane used, and the type and the molecular weight of segments as described above.

A suitable thickness of the phase-separated membrane is about 5 to 50 μm, preferably about 10 to 30 μm. When the thickness is thinner than 5 μm, the membrane strength is markedly weakened and the membrane formation also becomes difficult. Also, when it is thicker than 50 μm, the permeability of the drug, etc. is reduced.

Such a phase-separated membrane is prepared by, for example, the following method. That is, the heat-melted segmented polyurethane is mixed, while stirring, with an aqueous solution of gelatin and a crosslinking agent at a predetermined proportion and, after defoaming, the mixture is spread in a predetermined thickness on a base film having a good peeling property, and dried for about 2 days at an ordinary temperature. The temperature for heat-melting varies depending upon the segmented polyurethane, gelatin and the crosslinking agent used, but the heat-melting is generally conducted at 50° to 80° C., preferably 55° to 70° C. The method for defoaming is not limited and, generally, is effected by, for example, an application of ultrasonic wave or defoaming under reduced pressure. The base film having a good peeling property is not specifically limited, but a synthetic resin film such as polyethylene terephthalate (PET), polymethyl methacrylate (PMMA), and the like, is used. The drying method is not specifically limited and may be conducted under atmospheric pressure or reduced pressure. However, in order to ensure the quality of the phase-separated membrane to be produced, the drying is preferably conducted in a clean room at a constant temperature of 23° C. and a constant humidity of 65%. In the above-described production method, a proportion of gelatin and the segmented polyurethane is 4:6 to 8:2, preferably 6:4 to 8:2, and an amount of the crosslinking agent to be incorporated is from 2 to 5 parts by weight, preferably about 3 parts by weight, per 100 parts by weight of gelatin.

In some instances, glycerin or polyglycerin (di-, tri-, tetra- or hexaglycerin, etc.) may be dissolved in the aqueous solution of gelatin. When such an agent is incorporated, it acts as a moisture absorbing agent, and a phase-separated membrane having a relatively dry feeling when it is in a dried state but having tackiness with a moisture retention property can be obtained. The amount of glycerin or polyglycerin to be incorporated is suitably from 20 to 60 parts, preferably from 30 to 50 parts, per 100 parts of gelatin. Glycerin or polyglycerin is dissolved in gelatin and the segmented polyurethane in the step of mixing and stirring and, therefore, contained in both of the gelatin phase 5a and the segmented polyurethane phase 5b after the phase-separation.

The raw material gelatin used can be a commercially available material or that is produced by a known method, and a desalted alkali gelatin which has been subjected to an alkali-treatment can be preferably used. Gelatin is a polypeptide obtained by decomposition and purification of collagen of animal skin or bone origin, and the alkali-treatment as referred to above means decomposition of collagen by soaking it in an alkali such as lime. Gelatin also includes an acid-treated gelatin, but the acid-treated gelatin is brittle due to its weak strength and thus is not suitable.

Further, as a crosslinking agent for gelatin, formalin or glutaraldehyde is conventionally known, but a di- and/or polyepoxy type crosslinking agent having a relatively long spacer is suitably used in the present invention since it is low in toxicity, is capable of forming a large crosslinked network chains of gelatin and is liable to form a flexible membrane. Examples of such crosslinking agents include polyethylene glycol diglycidyl ether, polypropylene glycol diglycidyl ether, neopentyl glycol diglycidyl ether, 1,6-hexanediol diglycidyl ether, glycerol polyglycidyl ether, trimethylolpropane polyglycidyl ether, diglycerol polyglycidyl ether, polyglycerol polyglycidyl ether, etc. Gelatin is crosslinked by the reaction between the epoxy group in these crosslinking agents and the constituting molecule of gelatin, for example, an amino group.

On the other hand, as the segmented polyurethane, a heat-sensitive and water-sensitive polymer represented by the above general formula can be suitably used as such. As described above, such a polymer makes it possible to adjust and select the type of the alkylene oxides constituting the segment, molecular weight, copolymer type, the proportion of EO in the copolymer, terminal groups, diisocyanates, and the total molecular weight of the polymer. Also, the melt viscosity, the degree of hydrophilic or hydrophobic (lipophilic) property and interactions can be adjusted thereby and thus the rate of diffusion or transfer and the penetration amount of drugs can be strictly controlled. This segmented polyurethane may be either the same as the one constituting the drug-storing layer of the present invention or different therefrom, so long as it is represented by the above general formula: R—A—(U)—F—(U)—B—R', though it is generally preferable to use the same one.

The phase-separated membrane as described above may be reinforced with a fiber net and the like, if necessary. Examples of the fiber net include synthetic resin fibers such as polyamide fibers and polyester fibers. In reinforcing with a fiber net, a fiber net can be soaked in the above-described preparation solution containing a segmented polyurethane, gelatin and the crosslinking agent and, after lightly squeezing the net to such a degree that openings of the net are filled even after drying the openings of the net, the net can be dried by spreading on a substrate film having a good peeling-off characteristic. The drying may be performed in accordance with the above-described method. The thickness of this reinforced membrane is from 100 to 250 μm in the fiber net part and from 5 to 50 μm in the phase-separated membrane part.

The drug to be contained in the drug-storing layer of the present invention is not particularly restricted, as long as it can be transdermally absorbed. The objects of the present invention can be achieved by using either a hydrophilic drug or a lipophilic one, or either a solid drug or a liquid one. Examples of the drug include the following compounds.

a) Prostaglandins (PG) (for example, PGA, PGD, PGE, PGF, PGI, 6-keto-PGE, 6,9-nitrilo-PGI$_1$, 6,9-methano-PGI$_2$, derivatives thereof, etc.).

b) Vasodilators (for example, nitroglycerin, etc.).

c) Corticosteroids (for example, hydrocortisone, betamethasone, etc.).

d) Antiinflammatory agents (for example, indomethacin, ibuprofen, etc.)

e) Antibiotics (for example, penicillin, erythromycin, etc.).

f) Hypnotic sedatives (for example, phenobarbital, etc.).

g) Anesthetic agents (for example, benzocaine, etc.).

h) Antimicrobial agents (for example, pentamycin, etc.).

i) Vitamins (for example, vitamin A, etc.)

j) Anticonvulsives (for example, attopine, etc.).

k) Hormones (for example, testosterone, etc.).

The content of each of these drugs in the base may be appropriately determined depending on the efficacy of the drug, the age and conditions of a patient, the desired therapeutic effects, the application site and the desired period of sustained release.

Action

The transdermal absorption preparation of the present invention comprises the above-described segmented polyurethane as the base of the drug-storing layer 4 and the above-described phase-separated membrane as the drug-releasing controlling membrane 5 (drug permeation membrane) and, therefore, has the following action and effect.

(1) The above-described polymer is a crystalline or paste-like solid at ordinary temperature below 30° C., and is capable of stably storing a physiologically active agent which is easily deteriorated by air, moisture or heat (e.g., a prostaglandin, an antibiotic, a vitamin, an abortion-inducing agent, a hypnotic, a sedative, a tranquilizer, an anticonvulsant, a muscle relaxant, an antiparkinsonian agent, an analgesic, an antipyretic, an anti-inflammatory agent, a local anesthetic, an anti-ulcer agent, a microcidal agent, a hormone, an androgen steroid, estrogen, a sympathetic stimulating agent, a cardiovascular agent, a diuretic agent, carcinostatic and anticancer agents, an antihypoglycemic agent and nutrients) in the drug-storing layer 4. In particular, the drug which is solid at ordinary temperatures does not undergo transfer during the storage.

(2) Since the base polymer of the drug-storing layer 4 easily becomes a liquid having a low viscosity at a temperature near the skin temperature of the living body, which is an amphipathic liquid in which both the water-soluble or hydrophilic segment and the hydrophobic segment exist together, it completely dissolves most of the drugs which are solid at ordinary temperatures if its amounts is a relatively small amount but can take effect and uniformly disperses the drug in a molecular state at the portion of the segment having a high affinity to the drug. Accordingly, in most of the cases, a solvent is not necessary for dissolving the drug in the polymer, and thus a means for completely evaporating the solvent is not required and a possible risk caused by the toxicity of the residual solvent can be avoided.

(3) When the liner 6 is peeled off and the transdermal absorption preparation is applied onto the skin, the segmented polyurethane phase of the phase-separated membrane (drug-releasing controlling membrane 5) is liquefied due to the skin temperature and easily dissolved in a small amount of water exuding from the skin. Further, the gelatin phase of the phase-separated membrane swells with water. Also, the segmented polyurethane serving as the base in the drug-storing layer 4 is melted and dissolved to become a liquid due to the skin temperature and water.

If a drug is dispersed in a system where both of the drug and the base are solids, there arises no distribution of the drug to the membrane. If either the drug or the base or both are liquid, the drug is distributed between the membrane and the base polymer in a closely contacted state. Namely, when the base comes in contact with the phase-separated membrane, the drug concentration in the base is not the same as that in the membrane and a gradient in the concentration of the drug occurs between them. However, in the system of the present invention comprising the solid base and the solid drug for stabilizing the drug and preventing it from transfer toward the surface during storage, the polymer is liquefied due to the skin temperature and water upon application and then, transfer of the drug onto the membrane becomes possible for the first time. In this system, therefore, the distribution coefficient from the base to the membrane is an important factor for membrane permeation. More specifically, when Km stands for the distribution coefficient to the membrane, ΔC stands for the difference in the concentrations between the front surface and the back surface of the membrane, Cv stands for the concentration in the base, Dm stands for the diffusion coefficient, and hm stands for the membrane thickness, the permeation amount Jm is represented by the formula:

$$Jm = \frac{Km \cdot Dm \cdot Cv}{hm} = Kp\Delta C$$

wherein Kp is the permeation coefficient. That is, the permeation amount is determined by the concentration of drug and the distribution coefficient in the base. In the phase-separated membrane, the segmented polyurethane represented by the above general formula R—A—(U)—F—(U)—B—R', which is either the same as the base or different therefrom, is buried in the membrane as a microphase. Accordingly, it is fluidized as a liquid, and leaked out of the membrane and transferred to the skin. This fact indicates that the distribution coefficient, i.e., the permeation coefficient greatly increases.

The viscosity of the molten segmented polyurethane is about 2,000 centipoise or less which is a low value as compared with the viscosity of approximately 5,000 to 10,000 centipoise of the polymers described in the prior JP-A-63-108019 (U.S. Pat. No. 4,762,899) and JP-A-63-146812. Accordingly, the drug dissolved in the base polymer diffuses therein and is transferred to the skin side at a high proportion. The polymer is fluidized and transferred to the skin from the phase-separated membrane, and thus the efficiency of the drug to reach to the skin is improved. Such a system is effective for producing a transdermal absorption preparation having a high releasing ratio in which a drug is contained at a low concentration or a physiologically active substance is contained in a very minute amount of from several micrograms to several hundreds micrograms per prescription. The viscosity referred to herein means a viscosity measured by Brookfield type rotational viscometer using No. 4 rotor at a rotation of 60 r.p.m.

According to T. Higuchi (*J. Soc. Cosmetic Chemists*, 11, 85 (1960)), the releasing amount of the drug with respect to the release from a solution state has the following correlation at the initial stage:

$$M = 2Co \left( \frac{Dvt}{\pi} \right)^{1/2}$$

wherein:

M: Amount of drug released per unit area

Co: Initial concentration of drug in base

Dr: Diffusion coefficient of drug in base t: Time, if the releasing stage from the base material is a rate-determining step. That is, the releasing amount is proportional to the initial concentration, the diffusion coefficient and the time. When Co and t are constant, the releasing ratio depends on the diffusion coefficient. Thus, it would be understood that there is significance in the present invention where the viscosity of the melted base polymer is reduced for the purpose of increasing the diffusion coefficient.

Incidentally, according to the formula of Wilke (Wilke: *Chem. Eng. Progr.*, 45, 218 (1949), the diffusion coefficient in the liquid phase is indicated as follows:

$$D_L = 7.4 \times 10^{-8} \frac{(xM_2)^{1/2}T}{\mu_2 V_1^{0.6}}$$

wherein:

$D_L$: Diffusion coefficient (cm²/sec) of solute molecule at temperature T (°K) in a dilute solution comprising solvent 2 and solute 1

$M_2$, $\mu_2$: Molecular weight and viscosity (centipoise) of solvent x: Degree of association of solvent $V_1$: Molar volume at boiling point of solute Accordingly, it is understood from the above formula that the diffusion coefficient increases as the viscosity of solvent decreases. That is, it is well supported that as the viscosity of the base after melting decreases, the diffusion coefficient of the drug increases whereby the transfer to the skin side which is a low concentration side increases.

(4) Since an EO polymer is selected as a hydrophilic segment in the segmented polyurethane serving as the base of the drug-storing layer 4, its crystal is liquefied at once in response to heat. Also, the crystal is easily dissolved in water exuded from the living body, and the sensitivity to water is sharp. That is, the base easily dissolves a hydrophilic drug. However, since the polymer can be made amphipathic by using a hydrophobic segment as the other segment or using an alkoxy groups of an alkyl chain as the terminal groups, the degree of the affinity to a hydrophilic drug can be controlled, and the releasing ratio of a hydrophilic drug which is difficult to be absorbed by the skin can be improved.

(5) In the case of a transdermal absorption preparation of the present invention having a structure in which the segmented polyurethane of the base is molten and reached to and contacted with the surface of the skin through the drug-releasing controlling membrane 5, a less absorbable drug can be absorbed through the skin at a relatively effective way, since the segmented polyurethane can be made amphipathic and thereby exhibits good affinity to the lipids of the skin. Thus, it is not necessary to use an additional absorption enhancer.

(6) The segmented polyurethane of the base has a molecular structure similar to a polyalkylene glycol which has been conventionally used as an additive to drugs and cosmetics. For this reason, skin irritation and toxicity are substantially not observed, and the polymer is safe. Also, the polymer is safe since residual monomers do not exist, which is different from acrylic polymers.

(7) Although the viscosity of the segmented polyurethane of the base in a molten state is low to show advantage for diffusion, but is not so low that the polymer flows down from the skin upon application. The degree of the viscosity is that required for suitably spreading the base on the skin surface which is advantageous for absorption of the drug from the skin. The adjustment of such a melt viscosity has been achieved by adjusting the type and the molecular weight of the segments and the total molecular weight of the base polymer.

1: Surface layer.
2: Pressure-sensitive adhesive layer.
3: Hard base.
4: Drug-storing layer.
5: Drug-releasing controlling membrane (phase-separated membrane).
5a: Gelatin phase.
5b: Segmented polyurethane phase.
6: Liner.

BEST MODE FOR CARRYING OUT THE INVENTION

Examples of the present invention are hereinafter described.

[EXAMPLE 1]

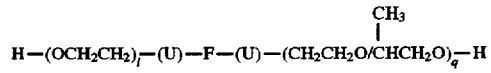

wherein a number average molecular weight of polyethylene oxide is 1,000, a number average molecular weight of the random copolymer (EO/PO=1/1; on the molar basis) is 400, (U) represents a urethane bond, and F represents —(CH$_2$)$_6$—.

Figure 1:
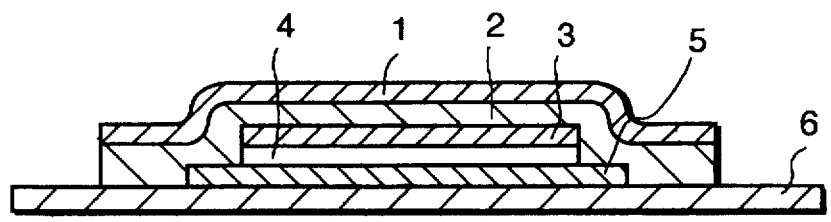
FIG. 1 is a sectional view which shows an example of the fundamental structure of the transdermal absorption preparation according to the present invention.
Figure 2:
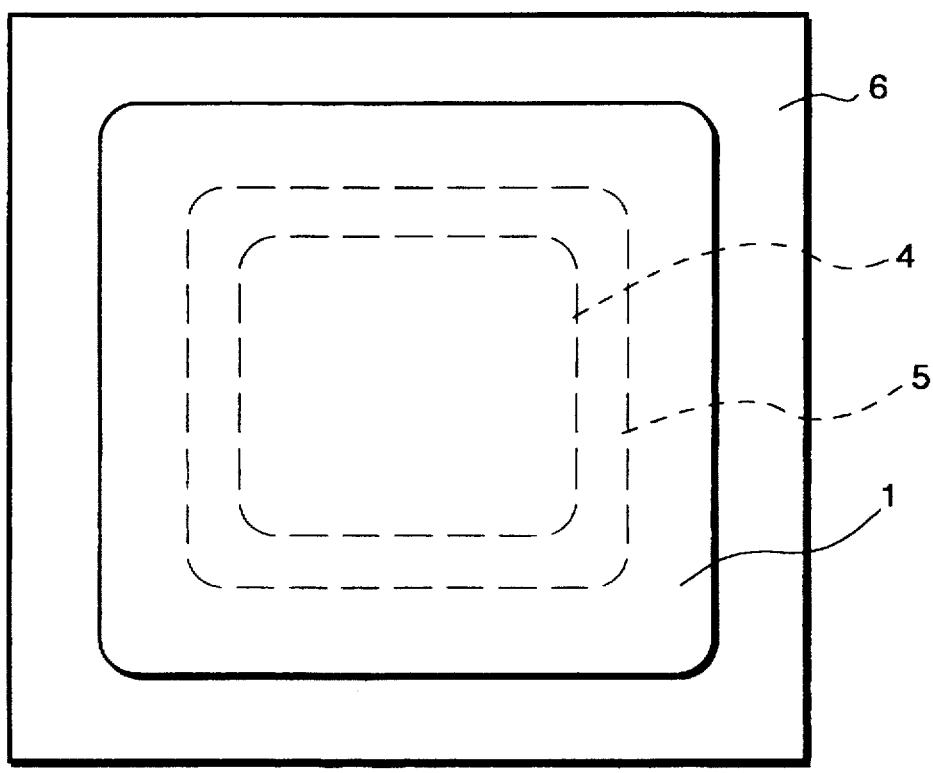
FIG. 2 is a top view which shows an example of the fundamental structure of the transdermal absorption preparation according to the present invention.
Figure 3:
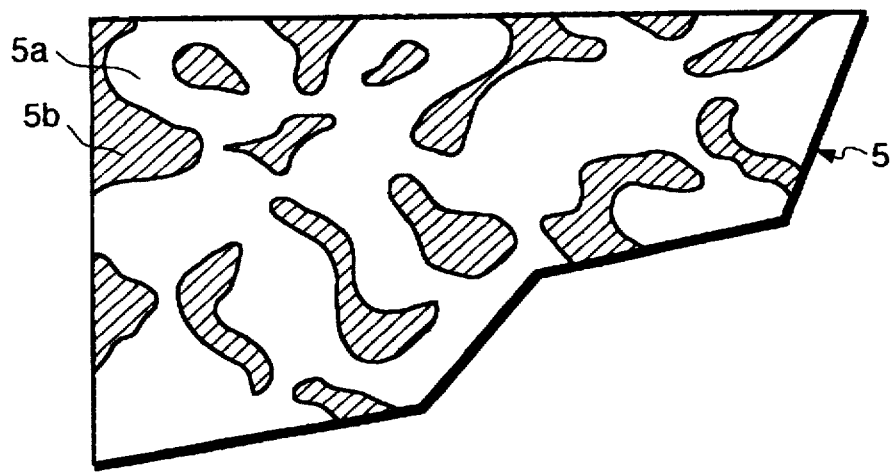
FIG. 3 is a partial top view which shows a phase-separated membrane to be used as a drug-releasing controlling membrane.

A polymer (m.p.: 35.0° to 35.6° C.) represented by the above structural formula, which was in the form of a soft wax at ordinary temperatures, was heated to 60° C. to thereby give a transparent liquid polymer having a low viscosity (about 1,000 cps). Then, prostaglandin E$_1$ (PGE$_1$) was added thereto in such an amount as to give a weight ratio (PGE$_1$/polymer)=(2.4/97.6) and homogeneously dissolved by stirring to give a transparent liquid. This drug which has the melting point of 120° C. was completely dissolved in the polymer. Then, the solution was solidified by cooling it to an ordinary temperature (lower than 30° C.) and employed as a drug-storing layer. The constitution of the preparation was as shown in FIGS. 1 and 2. That is, a 1,2-polybutadiene foam (expansion ratio: 5, thickness: 400 μm, 3.5×3.5 cm square) was used as a surface layer. An acrylic adhesive was applied in a thickness of about 50 μm onto one face of this surface layer. To the resulting adhesive face at the center of the base material, a hard base of a polyester film (thickness: 100 μm, 2×2 cm square) was adhered. Then, the polymer containing PGE$_1$ was overlaid as the drug-storing layer on this film and spread in a thickness of 35 μm and 1.5×1.5 cm square. Next, a phase-separated membrane, which comprised the above-described gelatin and the same segmented polyurethane as the one employed in the above drug-storing layer (polymer/gelatin=30/70 wt. %, thickness: 20 μm, 2.5× 2.5 cm square), was overlaid in such a manner as to cover the drug-storing layer. The phase-separated membrane was produced by mixing under stirring the segmented polyurethane in a molten state with a 5% aqueous solution of gelatin and a crosslinking agent (glycerol polyglycidyl ether) at a weight ratio of 2.4/97.45/0.15, defoaming the resulting mixture and spreading it onto a polyethylene terephthalate film in a thickness of 600 μm followed by drying in a clean room at 23° C. and a humidity of 65% for 2 days. Further, a silicone-treated mold-release paper was adhered thereto as a liner and thus the preparation was completed. This preparation contained 200 μg/sheet of the drug.

This preparation was introduced into a moistureproof aluminum-deposited film bag for packaging and sealed therein together with silica gel in vacuo. After storing at a temperature lower than 25° C. for 1 year, the preparation was taken out from the bag again. Then, the content of the drug was measured and compared with that before storage to thereby examine the stability of the drug. As a result, almost no change was observed, which proved excellent storing stability. After peeling off the liner, the preparation was applied onto the human skin at the inside of an upper arm and the amounts of the drug thus absorbed transdermally was calculated by measuring the amount of the drug remaining in the preparation and that on the skin surface by liquid chromatography. The amount of the drug remaining on the skin surface was recovered by wiping the skin surface with gauze, absorbent cotton, or the like and then soaking them in a solvent such as ethyl alcohol, etc. to thereby extract the drug. Similarly, the drug remaining in the preparation was recovered by soaking the preparation in a solvent such as ethyl alcohol, etc. to thereby extract the drug. As a result, it was found that 20 μg, 40 μg, 60 μg and 80 μg of the drug had been transdermally absorbed into the body respectively after 6, 12, 18 and 24 hours, which suggests that the drug was released almost on the 0 order. Although no absorption enhancer was employed in this case, it was proved that the drug was transdermally absorbed at a high ratio as a preparation containing a minute amount of the active ingredient. Also, this preparation was not irritative to the skin. Therefore, it had sufficient practical value.

[EXAMPLE 2]

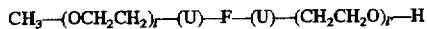

wherein a number average molecular weight of methoxypolyethylene oxide in the left segment of the molecular structure is 400, a number average molecular weight of polyethylene oxide in the right segment is 1,000, (U) represents a urethane bond, and F represents a structure of the moiety of hydrogenated 2,4-toluylene diisocyanate (hydrogenated TDI) excluding two isocyanate groups.

Similar to the procedure of Example 1, prostaglandin $E_1$ was dissolved in a polymer represented by the above structural formula, which was in the form of a wax at ordinary temperatures (m.p.: 36°–37° C.), provided that a small amount of ethanol was added for facilitating the dissolution. Then, the ethanol was removed by evaporation under reduced pressure.

Next, a preparation was manufactured in the same manner as the one employed in Example 1 and the amount of the drug transdermally absorbed was monitored. As a result, a sustained release pattern on the 0 order was also observed in this case and about 75 μg of the drug had been transdermally absorbed after 24 hours. Although no absorption enhancer was employed in this case too, the absorption ratio was relatively high as a preparation containing a minute amount of the active ingredient and thus the preparation had sufficient practical value.

[EXAMPLE 3]

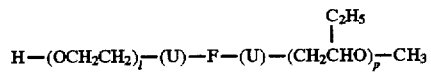

wherein a number average molecular weight of polyethylene oxide is 1,000, a number average molecular weight of metoxypolybutylene oxide is 600, and F represents —$(CH_2)_6$—.

Similar to the procedure of Example 1, prostaglandin $E_1$ methyl ester ($PGE_1$ methyl ester) was dissolved in a polymer represented by the above structural formula and a phase-separated membrane was adhered thereto, thus giving a preparation. This preparation also achieved favorable results in an application test. It showed a release pattern on the 0 order and the transdermal absorption ratio reached about 50% after 48 hours.

[EXAMPLE 4]

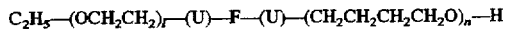

wherein a number average molecular weight of polyethylene oxide ethyl ether is 1,000, a number average molecular weight of polytetramethylene oxide is 600, and F represents a structure of the moiety of the isophorone diisocyanate excluding two isocyanate groups.

A crystalline waxy polymer represented by the above structural formula was heated to 60° C. to thereby give a transparent liquid polymer having a low viscosity. Then, testosterone was added thereto as a drug in such an amount as to give a weight ratio (testosterone/polymer)=(0.5/99.5) followed by thoroughly stirring. Although this drug has a melting point of 153° to 157° C., the complete dissolution of the drug was confirmed by microscopic observation. Then, a transdermal absorption preparation was manufactured in the same manner as in Example 1. This preparation was applied onto the human skin and the drug releasing ratio was measured. The drug releasing ratio after 48 hours was about 40%.

[EXAMPLE 5]

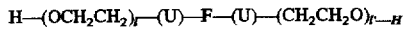

wherein number average molecular weights of polyethylene oxides are 1,000 and 400, and F represents —$(CH_2)_6$—.

A crystalline waxy polymer represented by the above structural formula was heated to 40° C. to thereby give a transparent liquid polymer having a low viscosity. Then, betamethasone sodium phosphate (dexamethasone sodium phosphate) was added thereto as a drug in such an amount as to give a weight ratio (betamethasone sodium phosphate/polymer)=(1.0/99.0) followed by thoroughly stirring. Then, a transdermal absorption preparation was manufactured in the same manner as in Example 1. This preparation was applied onto the abdominal skin of a rat and the releasing property of betamethasone sodium phosphate was examined. As a result, it showed a favorable releasing performance.

[EXAMPLE 6]

A polymer represented by the structural formula of the above Example 1 was used and $PGE_1$ was added thereto in such an amount as to give a weight ratio ($PGE_1$/polymer)= (2.4/97.6) to prepare a drug-storing layer by the same manner as in Example 1. As a phase-separated membrane, a mixture of the polymer/gelatin/glycerin (25/55/20, wt. %) was shaped into a membrane and adhered to the above-described drug-storing layer in the same manner as in Example 1 to thereby give a preparation. This preparation was applied to the human skin and the transdermal absorption was measured. As a result, the drug was released in almost the same amount as that of Example 1.

[Comparative Example 1]

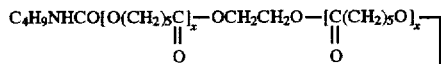

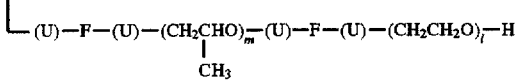

wherein a number average molecular weight of poly ε-caprolactone is 530, a number average molecular weight of polypropylene oxide is 400, a number average molecular weight of polyethylene oxide is 1,000, (U) represents a urethane bond, and F represents —(CH$_2$)$_6$—.

A polymer represented by the above structural formula is that described in Example 2 of JP-A-63-146812 and having a melting point of 36° to 37° C. The same drug as used in Example 1 of the present invention was dissolved in this polymer in the same amount and by the same method as those of Example 1 to thereby give a transdermal absorption preparation. Similarly, this preparation was applied to human skin. As a result, only a relatively small amount (less than 30 μg) of the drug was transdermally absorbed after 24 hours. It is considered that one of the major reasons therefor resides in the fact that this polymer had a high melt viscosity and thus only poor diffusion and transfer of the drug were achieved.

[Comparative Example 2]

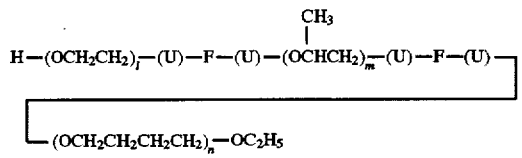

wherein a number average molecular weight of polyethylene oxide is 1,000, a number average molecular weight of polypropylene oxide is 400, a number average molecular weight of polytetramethylene oxide is 650, (U) represents a urethane bond, and F represents —(CH$_2$)$_6$—.

A polymer represented by the above structural formula is that described in Example 3 of JP-A-63-146812. The same drug as used in Example 1 of the present invention was dissolved in this polymer in the same amount and by the same method as those of Example 1. Next, the obtained solution was solidified by cooling to an ordinary temperature lower than 30° C. to thereby give a drug-storing layer. A preparation of the same constitution with that of Example 1 of the present invention was manufactured but using a reactivating gelatin membrane (thickness: 20 μm) described in Example 3 of JP-A-63-146812 was used as a drug-releasing controlling membrane. Then, this preparation was applied to human skin at the inside of an upper arm and the amount of the drug transdermally absorbed was measured. As a result, the drug was absorbed only in a small amount (i.e., 9 μg, 15 μg, 20 μg and 24 μg respectively after 6, 12, 18 and 24 hours), thus showing a poor absorption ratio. It is considered that the reasons therefor reside in that the polymer in the drug-storing layer of this Comparative Example had a high melt viscosity, compared with the preparation of the present invention, and thus only poor diffusion and transfer of the drug were achieved, and that the reactivating gelatin membrane used as the drug-releasing controlling membrane had a low drug-permeability.

Figure 4:
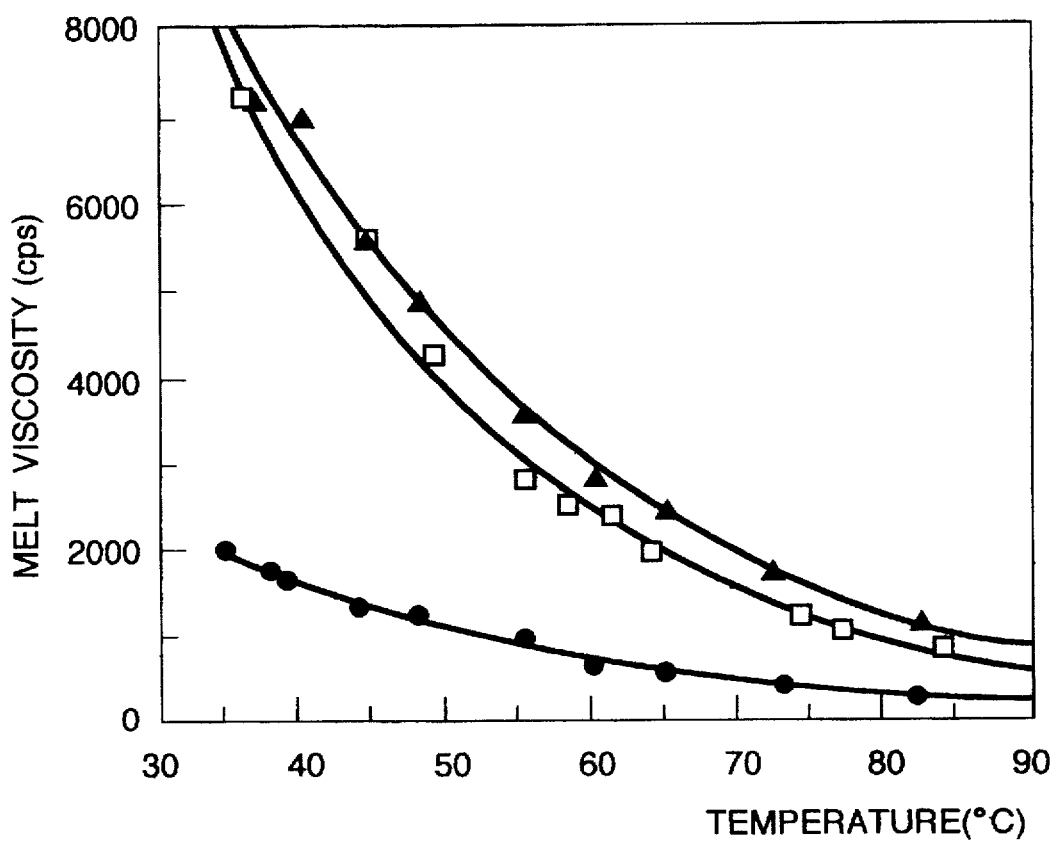
FIG. 4 is a graph which shows the relationship of the melt viscosity and temperature regarding each of the base polymer to be used in the present invention (the polymer of Example 1), the polymer described in Example 2 of JP-A-63-146812 and the polymer described in Example 3 of JP-A-63-146812.

Thus, the melt viscosities of the polymer of Example 1 of the present invention and the polymers of Examples 2 and 3 of JP-A-63-146812 were measured. FIG. 4 shows the results. As described above, these viscosities were measured by Brookfield type rotational viscometer using No. 4 rotor at a rotation of 60 r.p.m.

The polymers of Examples 2 and 3 of JP-A-63-146812 each shows a high melt viscosity of about 7,000 cps around its melting point followed by a slow decrease in viscosity with an increase in temperature. On the other hand, the polymer of Example 1 of the present invention shows a low melt viscosity of about 2,000 cps even around its melting point and a lower viscosity of 1,000 cps at about 60° C. The viscosities of these three polymers do not reach the almost same level until the temperature exceeds 100° C. These facts support that the low viscosity of the polymer of the present invention facilitates the diffusion and transfer of the drug and contributes to the increase in the transdermal absorption level.

Industrial Applicability

As is apparent from the above descriptions, in the transdermal absorption preparation of the present invention, the segmented polyurethane serving as the base of the drug-storing layer is solid at ordinary temperatures and becomes liquid at a temperature near the skin temperature of human. In addition, this polyurethane has a hydrophilic segment and heat-sensitive and water-sensitive characteristics. Also, it has a low melt viscosity and has properties which are advantageous to the dissolution and diffusion of the drug. Further, it has a property which is advantageous to the spreading on the surface of the skin. In addition, the phase-separated membrane employed as a drug-releasing controlling membrane makes it possible to control the diffusion rate and the permeation rate of the drug and the amount of the drug permeation. Accordingly, the transdermal absorption preparation of the present invention achieves a remarkable effect that the drug which has not been easily formulated in a transdermal absorption preparation (i.e., the drug which is solid at ordinary temperatures, water-soluble and less absorbable into the skin, takes effect with a small amount, has a short half-life and is liable to be decomposed) can be stored stably for a long period of time and, when applied to the skin, such a drug can be transdermally administered at a high releasing ratio and yet releasing slowly without irritation to the skin.

We claim:

1. A transdermal absorption preparation which comprises a drug-storing layer containing a drug and having a drug-releasing face coated with a drug-releasing controlling membrane, wherein said drug-storing layer comprises as a base a heat-sensitive segmented polyurethane represented by the general formula:

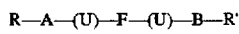

wherein A represents a polymer of ethylene oxide, propylene oxide, tetramethylene oxide or 1,2-butylene oxide, or a random or block copolymer thereof, B represents a random or block copolymer of ethylene oxide, propylene oxide, tetramethylene oxide and/or 1,2-butylene oxide. R and R', which may be the same or different, each represents a terminal H, $CH_3$, $C_2H_5$, $C_3H_7$ or $C_4H_9$. F represents a constituting structure which is a residual moiety of a diisocyanate compound excluding two isocyanate groups, and (U) represents a urethane bond, and at least one of A and B is hydrophilic and at the same time at least one of A and B has a characteristic that it melts near the temperature of human skin (30° to 40° C.);

wherein the viscosity of the seqmented polyurethane after melting is about 2,000 centipoise or less; and wherein said drug-releasing controlling membrane is a phase-separated membrane comprising a mixture of a crosslinked gelatin phase and an uncrosslinked segmented polyurethane phase.

2. A transdermal absorption preparation as claimed in claim 1, wherein A in the general formula is an ethylene oxide polymer.

3. A transdermal absorption preparation as claimed in claim 1, wherein B in the general formula is a random or block copolymer of ethylene oxide and propylene oxide.

4. A transdermal absorption preparation as claimed in claim 1, wherein A is an ethylene oxide polymer and B is a random or block copolymer of ethylene oxide and propylene oxide.

5. A transdermal absorption preparation as claimed in any of claims 1, 2, or 4, wherein a number average molecular weight of said ethylene oxide polymer is from 800 to 1,200.

6. A transdermal absorption preparation as claimed in claim 1, wherein a total molecular weight of said segmented polyurethane serving as a base of a drug-storing layer is a number average molecular weight of from 1,000 to 6,000.

7. A transdermal absorption preparation as claimed in claim 1, wherein glycerin and/or polyglycerin is contained in the drug-releasing controlling membrane.

8. A transdermal absorption preparation as claimed in claim 1, wherein said diisocyanate is a diisocyanate selected from the group consisting of p-phenylene diisocyanate, 2,4-toluylene diisocyanate, 4,4-diphenylmethane diisocyanate, naphthalene 1,5-diisocyanate, hexamethylene diisocyanate, tetramethylene diisocyanate, lysine diisocyanate, xylylene diisocyanate and hydrogenated 2,4-toluylene diisocyanate, hydrogenated 4,4-diphenylmethane diisocyanate, dicyclohexyldimethylmethane p,p'-diisocyanate, and isophorone diisocyanate.

\* \* \* \* \*

UNITED STATES PATENT AND TRADEMARK OFFICE
CERTIFICATE OF CORRECTION

PATENT NO.   : 5,723,145
DATED        : March 3, 1998
INVENTORS    : Yasuo SHIKINAMI
               Kunihiro HATA
               Seiei SASATANI
               Masao SUDOH It is certified that error(s) appears in the above-identified patent and that said Letters Patent is hereby corrected as shown below:

TITLE PAGE:

Please delete the Assignee "Takiron Co., Ltd., and Ono Pharamceutical Co., Ltd., both of Osaka, Japan"

Please correct the Assignee to read --Takiron Co., Ltd. of Osaka Japan--

Signed and Sealed this

Seventh Day of July, 1998

Attest:

BRUCE LEHMAN

Attesting Officer

Commissioner of Patents and Trademarks